(12) United States Patent
Kivi et al.

(10) Patent No.: US 8,019,433 B2
(45) Date of Patent: Sep. 13, 2011

(54) ADAPTIVE INTERFERENCE REDUCTION DURING TELEMETRY

(75) Inventors: Gary P. Kivi, Maple Grove, MN (US); Javaid Masoud, Shoreview, MN (US); Melvin P. Roberts, Chandler, AZ (US); Yuying (Mae) Chao, Vadnais Heights, MN (US); David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 810 days.

(21) Appl. No.: 12/109,576

(22) Filed: Apr. 25, 2008

(65) Prior Publication Data

US 2009/0270950 A1   Oct. 29, 2009

(51) Int. Cl.
*A61N 1/08* (2006.01)
*A61N 1/39* (2006.01)
(52) U.S. Cl. .................. 607/60; 607/5; 128/901
(58) Field of Classification Search .............. 607/4–5, 607/30–33, 59–61; 128/901
See application file for complete search history.

(56) References Cited

U.S. PATENT DOCUMENTS

| 4,374,382 | A | 2/1983 | Markowitz |
| 4,548,209 | A | 10/1985 | Wielders et al. |
| 6,411,064 | B1 | 6/2002 | Brink |
| 6,701,188 | B2 | 3/2004 | Stroebel et al. |
| 2003/0045906 | A1 | 3/2003 | Stroebel et al. |
| 2003/0045913 | A1 | 3/2003 | Stroebel et al. |
| 2007/0088398 | A1* | 4/2007 | Jacobson ............ 607/9 |
| 2007/0123946 | A1 | 5/2007 | Masoud |

FOREIGN PATENT DOCUMENTS

| EP | 0638986 | 2/1995 |
| WO | 9741923 | 11/1997 |

OTHER PUBLICATIONS

International Search Report, PCT/US2009/039497, 4 pages.

* cited by examiner

*Primary Examiner* — Carl H Layno
*Assistant Examiner* — Jessica Sarcione
(74) *Attorney, Agent, or Firm* — Michael J. Ostrom; Stephen W. Bauer

(57) ABSTRACT

An implantable medical device has a first module for performing telemetry communications with another device and a second module for delivering a high voltage therapy to a patient. The first module is configured to detect a communication error, and the second module is configured to determine a need for the therapy and to charge a capacitor in response to the need for the therapy. The second module is configured to suspend the capacitor charging in response to receiving a notification from the first module corresponding to detecting a communication error.

28 Claims, 3 Drawing Sheets

ADAPTIVE INTERFERENCE REDUCTION DURING TELEMETRY

TECHNICAL FIELD

The disclosure relates generally to implantable medical devices and, in particular, to a method and apparatus for reducing noise interference during telemetry communication between an implantable medical device and another device.

BACKGROUND

An implantable cardioverter defibrillator (ICD) delivers high voltage shock pulses to the heart to defibrillate or cardiovert the heart. One or more capacitors in the ICD are charged to a desired voltage to generate the shock pulses. Capacitor charging can cause noise interference that compromises telemetry communication between the ICD and another device, such as an external programmer or home monitor or another implanted device. Telemetry communication may be important during capacitor charging since a clinician may be trying to deliver a command to the ICD to abort the shock pulse delivery. Telemetry communication during capacitor charging also allows a clinician to observe real time data uplinked from the ICD relating to sensed and detected cardiac events. Accordingly, it is important to reduce the noise interference due to capacitor charging during telemetric communications in an ICD.

DETAILED DESCRIPTION

Figure 1:
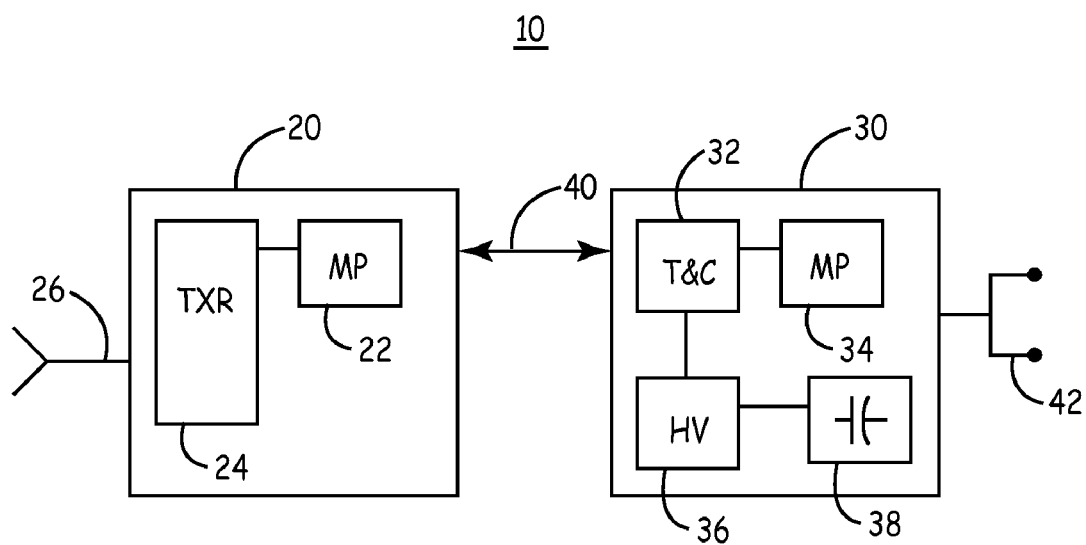
FIG. 1 is a functional block diagram of an ICD.

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a functional block diagram of an ICD according to one embodiment. ICD 10 includes a telemetry module 20 and a therapy module 30. Telemetry module 20 includes a microprocessor 22 and a transceiver 24 to enable bidirectional communication with an external device or another implantable device using antenna 26. Microprocessor 22 controls the telemetry operations.

Therapy module 30 includes a microprocessor 34 and timing and control circuitry 32 for controlling therapy delivery operations. High voltage charging circuitry 36 charges one or more capacitors 38 under the control of timing and control circuitry 32 whenever microprocessor 34 detects a need for therapy delivery. Microprocessor 34 may detect a need for therapy delivery based on a sensed cardiac rhythm or in response to a therapy delivery command received by telemetry module 20. Cardiac sensing and therapy delivery are performed using electrodes 42 coupled to ICD 10. Other components typically included in an ICD not shown in FIG. 1 include a battery, sensing circuitry, an A/D converter, physiological sensors, and so on, any of which may be included in various embodiments described herein for proper or application-specific ICD functioning as will be appreciated by one having skill in the art.

Telemetry module 20 and therapy module 30 communicate via command interface 40. Command interface 40 may be implemented according to numerous configurations, which may include hardware, software and firmware components. In one embodiment, hardware is implemented to send commands between the two modules 20 and 30 through a series of registers and buffers. Each module 20 and 30 includes firmware for generating requests and status commands to be communicated to each other via the command interface hardware. Command interface 40 is implemented for transmitting notifications between modules 20 and 30. According to embodiments of the present invention, telemetry module 20 and therapy module 30 are enabled to transmit notifications to the other module to notify the other module of a current operating status. In the embodiment shown, telemetry module 20 and therapy module 30 are implemented as two separate modules each having their own microprocessors 22 and 34 for controlling module functions. Thus, command interface 40 enables the separate modules to notify each other of an operating status, allowing the other module to respond by modifying its current operation status. It is recognized that embodiments of the present invention may also be implemented in an ICD architecture implementing telemetry and therapy delivery functions in modules that share a microprocessor.

Figure 2:
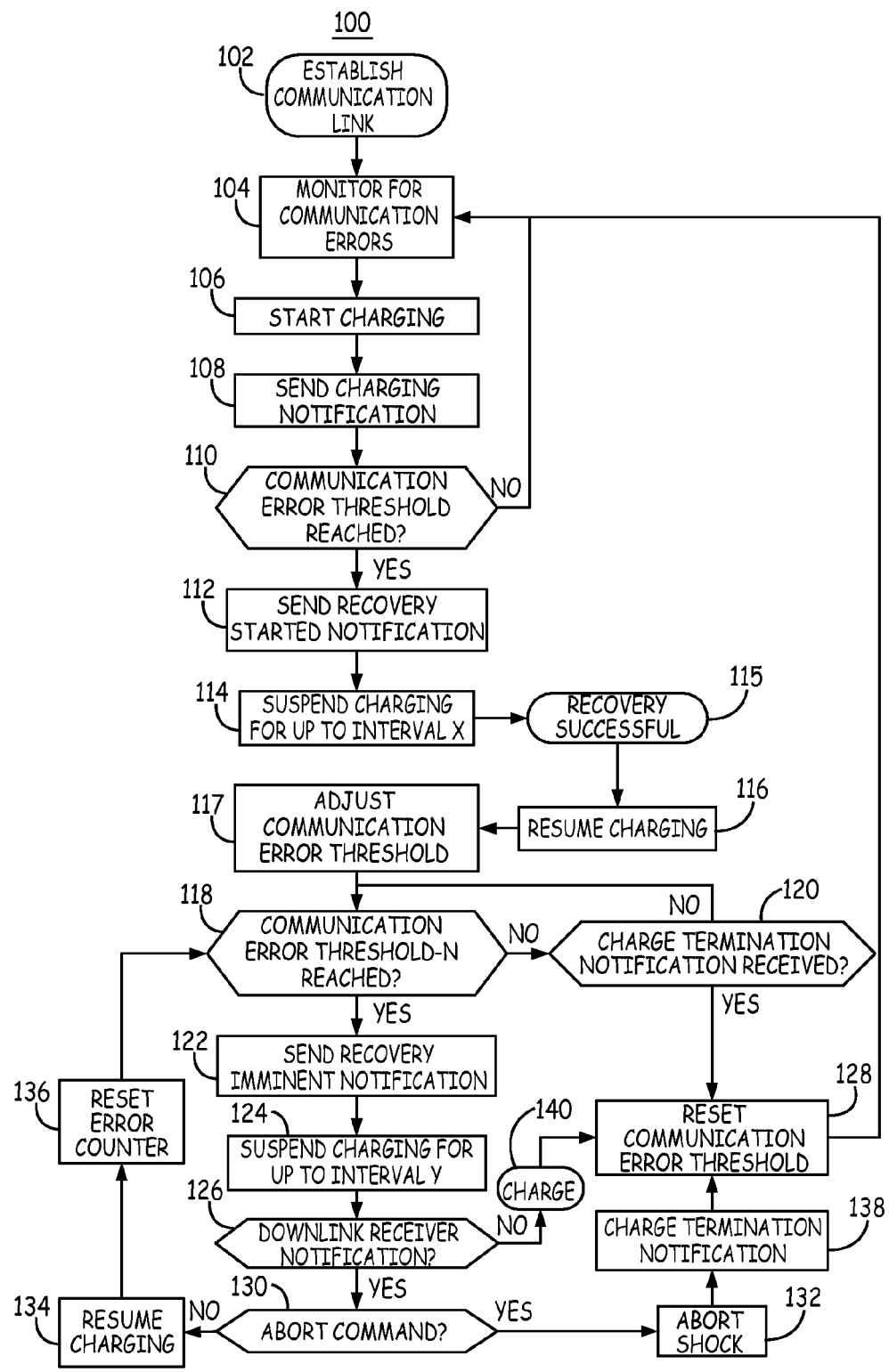
FIG. 2 is a flow chart of a method for adaptively reducing noise interference due to capacitor charging during telemetry communication.

FIG. 2 is a flow chart of a method for adaptively reducing noise interference due to capacitor charging during telemetry communication. Flow chart 200 is intended to illustrate the functional operation of the device, and should not be construed as reflective of a specific form of software, firmware or hardware necessary to practice the invention. It is believed that the particular form of software will be determined primarily by the particular system architecture employed in the device and by the particular telemetry and therapy delivery methodologies employed by the device. Providing software to accomplish the present invention in the context of any modern ICD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

In method 100, a communication link is established between the telemetry module of an ICD and another device, either another implantable device or an external device such as a programmer. The telemetry module monitors for communication errors at block 104 during the active communication link. In one embodiment, telemetry data is transmitted during time intervals referred to as frames. Frames for receiving downlink telemetry from another device and frames for transmitting uplink telemetry to the other device may alternate in a half duplex link. Data transmitted in each frame generally includes a preamble and a data packet. An invalid or "bad" downlink frame is a frame during which no valid preamble and downlink packet is received.

In one embodiment, a communication error detection threshold is defined as a predetermined number bad downlink frames. For example, when no valid preamble and downlink packets are received for two downlink frames a communication error is detected. As will be further described herein, a detected communication error causes the telemetry circuit to perform a channel recovery operation to restore successful communication. During a channel recovery operation, also referred to herein as a "communication recovery operation", one of the ICD and the other communicating device, such as an external programmer, transitions into a listen state while the other transmits to reestablish the communication link.

While the communication link is active, the therapy delivery module may initiate capacitor charging at block 106 in response to a need for delivering a high voltage shock. Capacitor charging can cause noise interference with the telemetry signals, particularly downlink telemetry signals being transmitted to the ICD, resulting in bad downlink frames. As such, the therapy module sends a notification to the telemetry module at block 108 via the command interface to notify the telemetry module that charging is in progress. At block 110, the telemetry module determines if the communication error threshold has been reached. The threshold may be defined as a number of bad downlink frames as described above. In alternative embodiments, a communication error threshold may relate to time intervals, noise amplitude, noise frequency or other noise parameters. In response to the communication error threshold being reached and the prior capacitor charging notification received by the telemetry module, the telemetry module sends a recovery started notification via the command interface to the therapy delivery module at block 112. In one embodiment, the recovery started notification is only sent if a capacitor charging notification has already been received. If a capacitor charging notification has not been received, the communication error detected at decision block 110 is unrelated to capacitor charging induced noise so the telemetry module performs communication recovery operations without notifying the therapy delivery module. However, if the capacitor charging notification has been received prior to detecting the communication error, the telemetry module sends a recovery started notification at block 112. The therapy delivery module responds at block 114 by suspending charging for up to a maximum time interval X. The maximum time interval X may be a predetermined interval selected to be long enough to allow the recovery operation to be successfully completed. The maximum time interval X may correspond, for example, to two consecutive cycles of downlink and uplink frames. Typically a recovery operation will be completed in less than the maximum time interval X and a recovery successful notification will be sent from the telemetry module to the therapy module at block 115. The capacitor charging will thus resume at block 116 immediately upon channel recovery (or upon expiration of maximum time interval X, whichever occurs earlier). Upon resuming capacitor charging, a capacitor charging notice may be delivered to the telemetry module at block 116, as will be further described in conjunction with FIG. 3.

In an alternative embodiment, the telemetry module sends a recovery started notification to the therapy delivery module every time channel recovery is started such that if capacitor charging is in progress, the therapy delivery module can suspend charging to allow channel recovery. In this embodiment, the telemetry module need not be notified in advance that capacitor charging is in progress.

At block 117, the telemetry module adjusts the communication error threshold in response to the charging resumed notification. Whenever a recovery operation is performed and a capacitor charging notice is received (either before or after the recovery operation is performed), the telemetry module adjusts the communication error threshold that would cause another recovery operation to be performed. Uplink communication (from the ICD to another device) is typically less affected by capacitor charging than downlink communication (from the other device to the ICD). As such, increasing the communication error detection threshold will allow uplink communication to be maintained for longer intervals without interruption even when downlink communication is compromised due to capacitor charging. Data transferred from the ICD during uplink communication can include EGM and Marker Channel data, which can be very useful to a clinician, as generally described in U.S. Pat. No. 4,374,382 (Markowitz), hereby incorporated herein by reference in its entirety. EGM and Marker Channel data displayed before and during capacitor charging and therapy delivery allow the clinician to evaluate the ICD function and performance. As such, it is desirable to maintain uninterrupted or minimally interrupted uplink communication during capacitor charging.

By adjusting the communication error threshold to a higher value, i.e. more bad downlink frames are allowed before starting a channel recovery operation, uplink telemetry can continue in the presence of compromised downlink telemetry. The increased communication error detection threshold also allows capacitor charging to continue with fewer interruptions, thereby preventing unacceptable prolongation of the capacitor charge time. In one embodiment the communication error threshold may be increased from two bad downlink frames to ten or more bad downlink frames, e.g. thirty bad downlink frames.

After the therapy module resumes charging, the telemetry module continues to monitor for a communication error based on the adjusted threshold. At block 118, the telemetry module detects when the adjusted threshold is almost reached, i.e. when a predetermined subthreshold number of communication errors are detected. For example, the telemetry module may detect when the threshold number of bad downlink frames less a predetermined number of frames N is reached. In one embodiment, the adjusted threshold is thirty bad downlink frames and N is two. As such, when twenty-eight bad downlink frames have been detected at block 118, a recovery imminent notification is sent by the telemetry module to the therapy delivery module at block 122.

The therapy delivery module continues charging the capacitor(s) until this subthreshold value is reached, unless the capacitor voltage has reached a targeted charge value. If charging is completed before a subthreshold number of communication errors are detected, a charge termination notification is sent by the therapy delivery module to the telemetry module. If a charge termination notification is received at block 120, the telemetry module resets the communication error threshold back to its nominal value at block 128. Method 100 returns to block 104 and continues to monitor for communication errors using the restored threshold value.

If the subthreshold value is reached at block 118, prior to a charge termination notification, the telemetry module sends a channel recovery imminent notification to the therapy delivery module at block 122. At block 124, the therapy delivery module suspends charging for up to a predetermined time interval Y in response to the recovery imminent notification. Capacitor charging is suspended to allow downlink telemetry to be received by the ICD. The time interval Y may be a predetermined maximum time interval and the same as the time interval X or a different time interval. In one embodiment, a maximum time interval Y is selected to allow at least two downlink frames to be received.

After receiving one or more downlink frames successfully, the telemetry module sends a downlink received notification to the therapy delivery module at block 126. This notification allows the therapy delivery module to immediately resume charging at block 134 as along as an abort command was not received during the successful downlink frames, as determined at block 130. At block 136, the telemetry module resets a bad downlink frame counter, referred to in FIG. 2 as an "error counter", to restart counting bad frames from zero again while capacitor charging continues. The telemetry module then continues monitoring for a communication error according to the adjusted communication error threshold by returning to block 118.

If an abort shock command is received during the successful downlink frames as determined at block 130, capacitor charging is terminated and the shock delivery is aborted at block 132. A charge termination notification is sent from therapy delivery module to telemetry module at block 138. The telemetry module resets the communication error threshold to its nominal value at block 128 and returns to block 104 to continue monitoring for communication errors.

In one embodiment, if the maximum time interval Y is reached without a downlink received notification at block 126, capacitor charging is resumed at block 140 and continues until charge completion. The telemetry module resets the communication error threshold at block 128 and returns to block 104.

According to method 100 the capacitor charging is maintained during an active communication link until a channel recovery operation is performed based on a nominal communication error detection threshold. After suspending charging during channel recovery operations a first time, an adjusted communication error detection threshold allows capacitor charging to be maintained for intervals of time even when bad downlink frames are received. The increased error detection threshold results in fewer interruptions to capacitor charging and uplink data transmission. This adjustment of the error detection threshold after an initial channel recovery operation performed during capacitor charging can be referred to as "adaptive noise interference management." Such adaptive noise interference management will result in shorter capacitor charge times than noise reduction methods that suspend charging whenever a telemetry communication link is active (even before a communication error is detected) or every time a channel recovery operation is performed based on a nominal error detection threshold.

Figure 3:
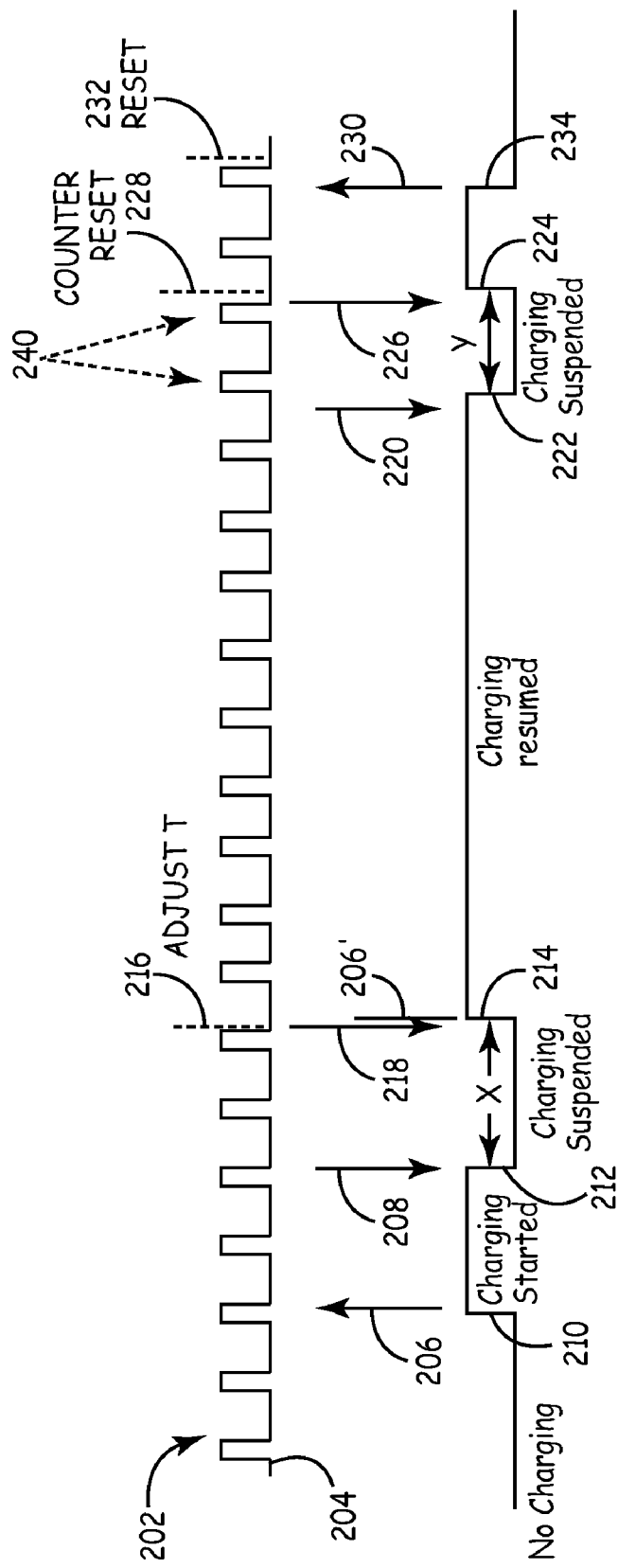
FIG. 3 is a timeline depicting operation of an ICD.

FIG. 3 is a timeline depicting operation of an ICD according to one embodiment of the invention. A telemetry communication link 202 is shown representing alternating intervals of sending (uplink) and receiving (downlink) frames. When link 202 is low, the ICD telemetry module is sending data to another device in an uplink transmission. Often, uplink transmission from the ICD to another device is not interrupted by noise caused by capacitor charging. When link 202 is high, downlink transmission from another device is sent to the ICD. The ICD may or may not successfully receive the downlink transmission depending on noise interference due to capacitor charging.

The events shown in FIG. 3 may be representative of testing and evaluation of the ICD during an office visit or a remote monitoring session. As such, the communication link 202 is established at a time 204 and maintained throughout testing, during which EGM and Marker Channel data may be uplinked from the ICD to an external device. At 210, capacitor charging is initiated in response to detecting a need for therapy, which may be receipt of a therapy delivery command received during downlink telemetry from the external device. The therapy delivery module sends a charge in progress notification at 206 to the telemetry module.

During charging, the telemetry link becomes compromised causing channel recovery to be initiated by the telemetry module. Channel recovery is initiated in response to detecting a communication error. As described previously, the communication error is detected in one embodiment when no valid preamble and downlink packets are received for a nominal number of downlink frames, e.g. at least two consecutive downlink frames. Same channel recovery is initiated to restore the communication using the same telemetry channel, i.e., frequency. In response to the communication error detection and the previously received charging notification 206 (with no intervening charge termination notification), the telemetry module sends a recovery in progress notification 208 to the therapy module. If the telemetry module has not received a previous charging notification 206, the telemetry module could initiation the channel recovery without notifying the therapy delivery module since no action would be needed by the therapy delivery module if capacitor charging is not ongoing at the time of the channel recovery operation.

In other embodiments, the therapy module does not notify the telemetry module that charging is in progress unless a channel recovery notification 208 has been received. In this alternative embodiment, charging may start at 210 without sending a notification 206. Upon detecting a communication error, the telemetry module starts the recovery operation and sends a notification 208 to the therapy module. The therapy module responds by suspending charging at 212 and then sending a charge in progress notification 206' back to the telemetry module when charging is resumed at 214. As such, the telemetry module is unaware of the capacitor charging status until the end of the recovery operation.

In either situation, the therapy module responds to the channel recovery notification 208 by suspending charging at 212 for up to a maximum interval of time X. The maximum interval X may be set to allow adequate time for the same channel recovery operation to be performed and may correspond to a desired number of downlink/uplink cycles, which would allow any pending downlink communication to be received by the ICD. In one embodiment, capacitor charging is suspended for a fixed interval of time, for example, up to 800 ms to allow channel recovery and down link communication. In an alternative embodiment, time interval X is variable up to a predetermined maximum such that charging is suspended only until the recovery operation is completed, which may occur sooner than the end of the predefined maximum time interval X. The time interval X is terminated immediately in response to a recovery successful notification 218 being sent from the telemetry module to the therapy module. The maximum time interval X is selected to avoid an excessive pause in capacitor charging which would lead to unacceptably long charge times. Acceptable charge times are generally less than approximately 5 to 10 seconds.

The telemetry module adjusts the communication error detection threshold at 216. The communication error detection threshold is increased in response to the initial recovery operation and receiving the charge notification 206 or 206' (received either at the onset of charging at 210 or upon resuming charging at 214 or any time there between). During channel recovery, both the capacitor charging and the uplink transmission of EGM and Marker Channel data are interrupted. The increased communication error detection threshold reduces the frequency of communication error detections and channel recovery operations. Hence, the adjusted communication error detection threshold effectively increases the time intervals that charging and uplink communication can be sustained without interruption, even in the presence of corrupted downlink communication. The sustained capacitor charging reduces undue prolongation of capacitor charge times otherwise caused by frequent charge suspensions during channel recovery operations. The adjusted communication error detection threshold also allows uplink transmission to be sustained more continuously, i.e. with fewer interruptions than would occur when frequent recovery operations are performed due to communication errors detected based on the nominal threshold. As such, capacitor charge times are kept within an acceptable time period, and uplink transmission of EGM data and Marker channel data is more continuous and complete.

The adjusted communication error threshold is generally increased to a higher number of bad downlink frames, e.g. any number of bad frames greater than the nominal threshold number, which is two in the above example. The adjusted threshold may be selected to correspond to a time interval or number of frames that is less than a time interval or number of frames during which another device will attempt delivery of a downlink command. For example, an external programmer may continue to attempt transmission of a command to abort a shock delivery for up to three seconds. The adjusted threshold is selected to cause channel recovery in less than three seconds such that corrupted downlink telemetry does not persist for longer than the attempted downlink transmission time. Thus the adjusted threshold is selected to assure a high probability of a command or other data that another device is trying to downlink to the ICD will have an opportunity to be successfully transmitted before the maximum time or number of attempts for downlink transmission is expired.

In one embodiment, once the adjusted threshold is reached, the recovery operation is initiated and a similar sequence of events beginning at notification 208 through charge suspension 212 for up to X ms is repeated. However, in other embodiments, the adaptive noise reduction methods avoid repeating channel recovery operations in order to avoid disrupting uplink telemetry. In the embodiment shown in FIG. 3, the telemetry module sends a recovery imminent notification 220 when a bad downlink frame count reaches a predetermined subthreshold value. The subthreshold value may be the adjusted threshold minus a predetermined number of frames, for example 1 to 3 three frames. Alternatively, the subthreshold value may be set as a truncated or rounded off percentage of the adjusted threshold, for example the nearest whole number to 90% of the adjusted threshold value.

In response to the recovery operation imminent notification 220, the therapy module suspends charging for a time interval Y at 222. Time interval Y may be predetermined and selected to be the same or different than time interval X. Generally, a maximum time interval Y is selected to allow a minimum number of downlink frames to be transmitted to promote assurance that any pending downlink commands are successfully received by the ICD. Upon receiving one or more valid downlink frames, the telemetry module sends a downlink received notification 226 to the therapy module. In one embodiment time interval Y is, for example, up to approximately 800 ms. In an alternative embodiment, time interval Y is a variable interval that is immediately terminated by the therapy module when a valid downlink received notification 226 is received from the telemetry module.

After receiving one or more downlink frames successfully, the telemetry module resets a bad downlink frame counter at 228. The adjusted communication error threshold value is maintained but the counter is reset to allow another interval of sustained capacitor charging and uplink telemetry, even in the presence of corrupted downlink telemetry as described above.

In response to the valid downlink notification 226, the therapy module resumes charging at 224, in the absence of receiving an "abort therapy" command. Upon reaching full capacitor charging, in accordance with a programmed shock pulse energy, the therapy module terminates capacitor charging at 234 and sends a charge termination notice 230 to the telemetry module.

In response to the charge termination notification 230, the telemetry module resets the communication error threshold (T) to its nominal value at 232. The telemetry communication link 202 may then continue with communication error detection based on the restored, nominal threshold value. As such, if another capacitor charging episode is started, channel recovery will be initiated based on the nominal detection threshold again.

If an "abort therapy" command is received during the successful downlink received while charging is suspended for interval Y, the therapy module responds by terminating charging immediately and canceling the shock delivery. A charge termination notification would then be sent from the therapy delivery module to the telemetry module immediately and the adjusted threshold would be reset to the nominal value.

Thus, an apparatus and method for controlling communication interference during capacitor charging in an ICD have been presented in the foregoing description with reference to specific embodiments. It is appreciated that various modifications to the referenced embodiments may be made without departing from the scope of the invention as set forth in the following claims.

The invention claimed is:

1. An implantable medical device, comprising;
    a first module for performing telemetry communications with a second device, the first module configured to detect a communication error;
    a second module for delivering a high voltage therapy to a patient, the second module configured to determine a need for the therapy and to charge a capacitor in response to the need for the therapy; and
    means for transmitting notifications between the first module and the second module,
    the second module configured to suspend capacitor charging in response to receiving a notification from the first module corresponding to detecting a communication error.

2. The device of claim 1 wherein the first module being configured to perform a communication recovery operation in response to detecting a communication error, wherein the notification corresponding to detecting a communication error is a notification that the recovery operation is being performed.

3. The device of claim 2 wherein the first module performs the communication recovery operation in response to detecting a nominal threshold number of invalid communication frames.

4. The device of claim 3 wherein the second module is configured to send a notification to the first module corresponding to capacitor charging in progress.

5. The device of claim 4 wherein the first module sends the notification that the recovery operation is being performed in response to the capacitor charging notification.

6. The device of claim 4 wherein the first module adjusts the threshold number of invalid communication frames to an adjusted threshold in response to the capacitor charging notification.

7. The device of claim 6 wherein the first module sends a notification to the second module prior to the adjusted threshold being reached, the notification corresponding to a recovery operation being imminent.

8. The device of claim 7 wherein the second module suspends the capacitor charging in response to the recovery operation imminent notification.

9. The device of claim 8 wherein the first module sends a notification to the second module corresponding to a valid downlink communication received.

10. The device of claim 9 wherein the second module resumes capacitor charging in response to the valid downlink communication received notification.

11. The device of claim 8 wherein the capacitor charging is suspended for an interval of time that is greater than a maximum time for receiving a downlink command from the second device.

12. The device of claim 6 wherein the second module sends a notification to the first module corresponding to capacitor charging termination.

13. The device of claim 12 wherein the first module resets the adjusted threshold to the nominal threshold in response to the capacitor charging termination notification.

14. The device of claim 6 wherein the adjusted threshold corresponds to a time that is less than a maximum attempted downlink transmission time from the second device.

15. A method for use in an implantable medical device, comprising;
  performing telemetry communications between a first module of the implantable medical device and a second device,
  charging a capacitor in response to a second module of the implantable medical device detecting a need for therapy delivery;
  detecting a communication error;
  transmitting a notification from the first module to the second module, and
  suspending the capacitor charging in response to the notification, the notification corresponding to detecting the communication error.

16. The method of claim 15 further comprising performing a communication recovery operation in response to detecting the communication error, wherein the notification corresponding to detecting a communication error is a notification of the recovery operation is being performed.

17. The method of claim 16 wherein the communication recovery operation comprises detecting a nominal threshold number of invalid communication frames.

18. The method of claim 17 further comprising sending a notification from the second module to the first module corresponding to capacitor charging in progress.

19. The method of claim 18 further wherein the notification that the recovery operation is being performed is sent from the first module to the second module in response to the capacitor charging notification.

20. The method of claim 18 further comprising adjusting the threshold number of invalid communication frames to an adjusted threshold in response to the capacitor charging notification.

21. The method of claim 20 wherein further comprising sending a notification from the first module to the second module prior to the adjusted threshold being reached, the notification corresponding to a recovery operation being imminent.

22. The method of claim 21 further comprising suspending the capacitor charging in response to the recovery operation imminent notification.

23. The method of claim 22 further comprising sending a notification from the first module to the second module corresponding to a valid downlink communication received.

24. The method of claim 23 further comprising resuming capacitor charging in response to the valid downlink communication received notification.

25. The method of claim 22 further comprising suspending capacitor charging for an interval of time that is greater than a maximum time for receiving a downlink command from the second device.

26. The method of claim 20 further comprising sending a notification from the second module to the first module corresponding to capacitor charging termination.

27. The method of claim 26 further comprising resetting the adjusted threshold to the nominal threshold in response to the capacitor charging termination notification.

28. The method of claim 20 wherein the adjusted threshold corresponds to a time that is less than a maximum attempted downlink transmission time from the second device.

* * * * *